United States Patent [19]

Ladislas et al.

[11] Patent Number: 5,411,978
[45] Date of Patent: May 2, 1995

[54] BENZISOTHIAZOLINONE-1-DIOXIDE DERIVATIVES AS ELASTASE INHIBITORS

[75] Inventors: Robert Ladislas, Santeny; Elemer Moczar, Gif Sur Yvette; William Georges Hornebeck, Versailles; Christiane M. Kerneur, Vitry Sur Seine, all of France

[73] Assignee: Chesebrough-Pond's USA Co., Division of Conopco, Inc., Greenwich, Conn.

[21] Appl. No.: 230,048

[22] Filed: Apr. 19, 1994

Related U.S. Application Data

[62] Division of Ser. No. 666,093, Mar. 7, 1991, Pat. No. 5,338,747.

[30] Foreign Application Priority Data

Mar. 8, 1990 [FR] France ................. 90 02951

[51] Int. Cl.⁶ ................. C07D 275/06; A61K 31/41
[52] U.S. Cl. ................. 514/373
[58] Field of Search ................. 514/373

[56] References Cited

U.S. PATENT DOCUMENTS

| | | | |
|---|---|---|---|
| 4,195,023 | 3/1980 | Mulvey et al. | 548/210 |
| 4,276,298 | 6/1981 | Jones et al. | 548/210 |
| 4,665,053 | 5/1987 | Robert et al. | 514/18 |

FOREIGN PATENT DOCUMENTS 0126009  11/1984  European Pat. Off. .

OTHER PUBLICATIONS

Journal of Biological Chemistry, vol. 255, No. 20, (1980), pp. 9848–9851.
Tetrahedron, vol. 29, pp. 3985–3986 (1973).
Journal of Biological Chemistry, vol. 256, No. 22 (1981) pp. 11603–11606.
Am. J. Respir. Cell. Mol. Biol., vol. 1, pp. 37–39 (1989).
Iowa State College J. Sci., vol. 12, (1937), p. 121.
Chemical Abstracts, vol. 78, Abstract No. 144282.
Chemical Abstracts, vol. 100, Abstract No. 191776 (1984).
Chemical Abstracts, vol. 51, No. 13, No. 9588de (1957).

*Primary Examiner*—Robert Gerstl
*Attorney, Agent, or Firm*—Milton L. Honig

[57] ABSTRACT

A composition is reported that includes an elastase inhibitor in a pharmaceutically or cosmetically acceptable carrier, the inhibitor being at least one benzisothiazolinone-1-dioxide derivative having the formula:

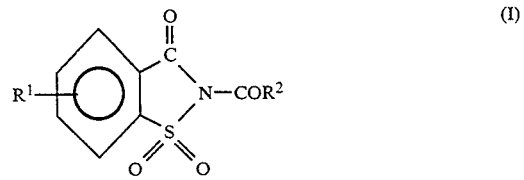

where $R^1$ is a hydrogen atom and $R^2$ is a monovalent $C_{12}$–$C_{20}$ alkyl or alkenyl group.

8 Claims, No Drawings

BENZISOTHIAZOLINONE-1-DIOXIDE DERIVATIVES AS ELASTASE INHIBITORS

This is a divisional application of Ser. No. 07/666,093 filed Mar. 7, 1991, now U.S. Pat. No. 5,338,747.

FIELD OF THE INVENTION

The present invention relates to benzisothiazolinone-1-dioxide derivatives that can be used as elastase inhibitors, and to compositions containing such inhibitors.

THE RELATED ART

It is well known that elastin is an elastic fibrous protein that occurs in the connective tissues of vertebrates. It is found in the walls of the blood vessels, the skin, lungs, cartilage, ligaments and other tissues. Elastin is the most durable protein in the body. Unfortunately but it suffers a particularly rapid degradation in all the elastin-rich tissues such as the vascular walls and the skin, in certain pathological conditions, as well as during the ageing process in general.

Elastin can be attacked only by certain proteases, called elastases or elastase-type proteases. These enzymes include pancreatic elastase and cell elastases, examples of the latter being leucocytic and platelet elastases, as well as the elastases found in macrophages, fibroblasts and the cells of the smooth muscles in the arteries. These enzymes can degrade the elastin in the tissues and organs mentioned above and so contribute to the development of disorders such as arteriosclerosis, emphysema, arthritis and diabetes, as well as to the ageing of the connective tissues in the body.

The activity of elastases is controlled and regulated by natural inhibitors present in the plasma (e.g. $\alpha$-1-antitrypsin and $\alpha$-2-macroglobulin) and in secretions from tissues (e.g. the bronchial secretion) [see e.g. W. Hornebeck et al., "Control of elastic tissue destruction by elastase inhibitors", in Deyl and Adam (eds.), Connective Tissue Research: Chemistry, Biology and Physiology, pp. 233–246, A.R. Liss Inc., New York, 1981].

Furthermore, numerous bacteria capable of entering the body secrete elastolytic proteases whose action greatly contributes to the pathogenic activity of these microorganisms.

It is also known that the growth of malignant rumours such as carcinomas and sarcomas, and the formation of metastases, which are often fatal to the patient, are also affected by the secretion of elastase-type proteases [see for example W. Hornebeck, D. Brechemier, G. Bellon, J. J. Adnet and L. Robert, "Biological Significance of Elastase-like Enzymes in Arteriosclerosis and Human Breast Cancer", in P. Straülli, A. J. Barrett and A. Baici (eds.), Proteinases and Tumor Invasion, vol. 6, ORTC Monograph Series, pp. 117–141, Raven Press, New York, 1980]. These enzymes can destroy the surrounding tissues and thus enable the malignant cells to enter the blood circulation, as a result of which the rumour can invade the body.

For all these reasons, it is important to possess inhibitors that can control the activity of elastases.

However, some elastases are useful or even indispensable for the body, for example when they digest the bacteria that have been destroyed by the phagocytic action of macrophages. It is therefore important to possess elastase inhibitors that act selectively in the elastic fibres whose integrity is indispensable for the proper functioning of the body.

The fact is that the enzymatic hydrolysis of elastin by elastases can be seen as a decisive factor in numerous disorders of the elastic tissues, such as arteriosclerosis, emphysema and certain skin diseases. In the living body, this proteolysis occurs when the balance is upset between the level of proteases with an elastolytic action and the level of natural inhibitors originating in the plasma or the tissues. One method proposed for the treatment of a genetic or functional deficiency of these protease inhibitors is to introduce natural inhibitors such as $\alpha$-1-antitrypsin as a replacement therapy.

However, the use of natural inhibitors has numerous disadvantages, including the cost of the treatment and the risk of adverse immunological reactions. Furthermore, the elastase inhibitors used in the experimental treatment of animals with emphysema are highly toxic.

Synthetic elastase-inhibitors have therefore been under investigation for some years now. Thus, U.S. No. 4,195,023 describes the use of 2-benzisothiazol-3-one derivatives and saccharin derivatives to inhibit elastases. The preferred compounds in that publication are derivatives substituted with a furoyl or a thenoyl group. The publication also gives some data for 2-(2-ethylbutyryl)-saccharin and 2-acryloylsaccharin. According to this document, the alkyl chain of the derivative contains at most 10 carbon atoms and is preferably branched, but the only example illustrated has a hydrocarbon chain with no more than five carbon atoms.

Although these inhibitors give satisfactory results, they are not sufficiently specific for the elastic fibres.

European Patent Specification EP-A 0 126009 describes some peptide derivatives that can be used as elastase inhibitors and are specific for elastic fibres. These derivatives are lipopeptides with a hydrophobic acyl group and a special peptide chain. However, these lipopeptides, which are consequently bifunctional, have the major disadvantage of containing a peptide moiety, which is susceptible to hydrolysis by other proteinases.

The aim of the present invention is therefore to incorporate into pharmaceutical or cosmetic compositions elastase inhibitors in the form of bifunctional benzisothiazolinone-1-dioxide derivatives with a) a hydrophobic chain that has an affinity for elastin and b) a moiety that is not a peptide group (so that it is more resistant to enzymatic hydrolysis) and which can also acrylate the active serine in the elastase.

SUMMARY OF THE INVENTION

The present invention therefore provides a composition comprising (i) an elastase inhibitor which is at least one benzisothioazolinone-1-dioxide derivative having the formula:

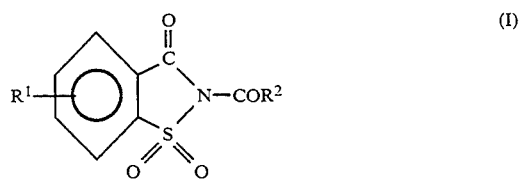

where
$R^1$ is a hydrogen atom or a $C_1$–$C_5$ alkyl or alkoxy group, and
$R^2$ is a monovalent $C_8$–$C_{20}$ alkyl or $C_9$–$C_{20}$ alkenyl group, optionally substituted with OH or COOH group,
$R^2$ is a group with the formula:

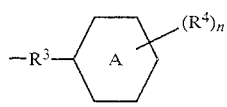

where
R³ is a divalent straight or branched C₂–C₆ saturated or ethylenically unsaturated aliphatic group

is an aromatic nucleus

R⁴ is OH, a $C_1$–$C_4$ alkyl or a $C_1$–$C_4$ alkoxy group n is zero or an integer in the range of 1–5, and when n > 1, the R⁴ groups can be different, or else R² is a group with the formula:

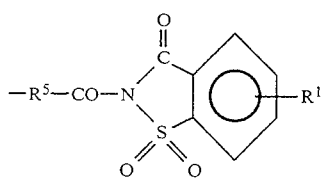 (III)

where
R¹ is the same as above, and
R⁵ is a divalent straight or branched $C_8$–$C_{20}$ saturated or ethylenically unsaturated aliphatic group, and (ii) a pharmaceutically or cosmetically acceptable carrier or vehicle.

DETAILED DESCRIPTION

A benzisothiazolinone-1-dioxide derivative of formula (I) above, which is the active ingredient of a composition as above, has two functional groups, namely a "lipid arm" (R² or part of R²), which has a high affinity for the elastic fibres in question, and the benzisothiazolinone-1-dioxide moiety, which can react with elastase in order to inhibit it.

Owing to the presence of this hydrophobic chain, the benzisothiazolinone-1-dioxide derivatives of the present invention can accumulate on the elastic fibres to be protected and therefore act exclusively or almost exclusively on the elastase located near these fibres. In view of this mode of action, it is possible to make the substance act specifically at the site of the target fibres to be protected, which ensures a more efficient inhibition of elastase.

The compounds according to the invention are therefore more efficient and more economical bifunctional inhibitors than the known synthetic inhibitors, which lack the functional group that has a special affinity for the elastic fibres present in the tissues to be protected.

The acylsaccharins described in U.S. Pat. No. 4,195,023, which have the formula:

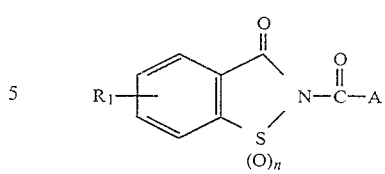 (II)

carry a hydrocarbon chain A with generally at most five carbon atoms, and this is not long enough to confer on the derivative either an affinity for elastin or an ability to occupy the hydrophobic site on elastase. As will be seen later, the affinity of the derivative for elastin and for the hydrophobic site on the elastase does not become detectable until the number of carbon atoms reaches nine, improving as the number reaches eleven and peaking when this number is 16.

As mentioned in the definition of the compounds according to the invention given above, a monovalent $C_8$–$C_{20}$ straight-chain or branched alkyl group can carry at least one substituent in the form of an OH or COOH group. If the monovalent alkyl is not substituted with these groups, it preferably contains 11 carbon atoms. Such examples of such alkyl groups include the nonyl, undecyl, tridecyl, pentadecyl, heptadecyl and nonadecyl groups, while COOH—(CH₂)₈— is an example of the substituted alkyl groups.

A monovalent $C_9$–$C_{20}$ alkenyl group is a monovalent alkylene group theoretically obtainable by removing a hydrogen atom from a carbon in an olefinic hydrocarbon. Such a group may contain a single ethylenic double bond or more than one ethylenic double bond. As before, these groups may be either unsubstituted or they may carry at least one OH or COOH group. Examples of such unsaturated groups are the dec-9-enyl, hepatadec-8-enyl, hepadeca-8,11-dienyl and the CH₃—(CH₂)₅—CHOH—CH₂—CH═CH—(CH₂)₇— group.

A divalent group R³ may in particular be a group theoretically obtainable by removing hydrogen from each of two terminal carbons in a straight-chain or branched alkane or alkene, examples being the —CH═CH— group, the —CH₂—CH₂— group and the —(CH₂)₃ group.

An aromatic nucleus, denoted

may comprise one or more benzene rings, examples being the groups obtained from benzene, anthracene, naphthalene, biphenyl, terphenyl, triphenylbenzene, indene, diphenylene, fluorene and phenanthrene.

A divalent group R⁵ may in particular be a group theoretically obtainable by removing a hydrogen atom from each of two terminal carbons in a straight-chain or branched $C_8$–$C_{20}$ alkane, alkene or polyalkene, as exemplified by the —(CH₂)₈— group.

Furthermore, R¹ can be a hydrogen atom or a substituent chosen from amongst $C_1$–$C_5$ alkyl or alkoxy groups. When R¹ is a substituent, it is desirably chosen such as to promote the hydrolytic opening of the heterocyclic ring. However, R¹ is generally a hydrogen atom.

As mentioned before, $R^2$ is the functional group that confers an affinity for the elastic fibres on the compound of the invention, owing to its lipophilic nature.

In the first embodiment of the invention, $R^2$ is a long-chain alkyl or alkenyl group whose long hydrocarbon chain confers a strongly lipophilic nature on the compound according to the invention. This facilitates its penetration into the skin and makes it suitable for cosmetic use.

In the second embodiment of the invention, $R^2$ is a group with the formula:

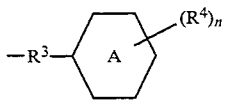
(II)

where
$R^3$ and $R^4$ are as defined before;
$R^3$ is preferably a divalent group obtained from an alkane

is a benzene ring
$R^4$ is a $C_1$–$C_4$ alkoxy group or a hydroxyl group, and n is 1 or 2.

These $R^2$ groups are exemplified by the 3,4-dimethoxycinnamoyl, cinnamoyl, dihydrocinnamoyl and pmethoxyphenylbutyryl radical.

In the second embodiment, the compound according to the invention is again lipophilic, this time because it comprises an aromatic nucleus.

In the third embodiment of the invention, $R^2$ has the following formula:

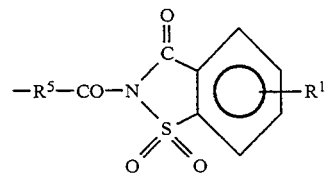
(III)

where
$R^1$ and $R^5$ are as defined before, but;
$R^1$ is preferably a hydrogen atom, and
$R^5$ is a divalent group obtained from an alkane.

In this case, this $R^5$ group confers on the compound both a lipophilic character and an affinity for the elastic fibres in question, while the presence of two benzisothiazolinone-1-dioxide rings increases the inhibitory activity.

The benzisothiazolinone-1-dioxide derivatives of this invention can be prepared by conventional methods in which the starting materials are an acid chloride and an alkali metal derivative of the corresponding benzisothiazolinone-1-dioxide.

Thus, it is possible to prepare the benzisothiazolinone-1-dioxide derivative of the invention, with the formula:

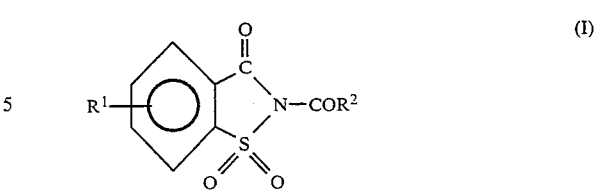
(I)

where
$R^1$ is a hydrogen atom or a $C_1$–$C_5$ alkyl or alkoxy group,
$R^2$ is an optionally substituted monovalent $C_9$–$C_{20}$ alkyl or alkenyl group,
$R^2$ is a group with the formula:

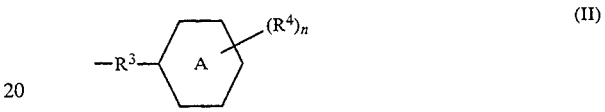
(II)

all as defined before by reacting an alkali metal derivative of benzisothiazolinone-1-dioxide having the formula:

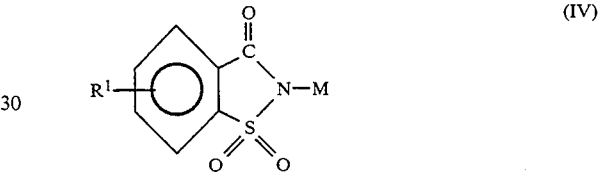
(IV)

where $R^1$ is as defined before, and M is an alkali metal with an acid chloride having the formula:

$R^2$—COCL  (V)

wherein $R^2$ is the same as before.

The benzisothiazolinone-1-dioxide derivative with formula I in which $R^1$ is as defined above and $R^2$ represents the group with formula (III)

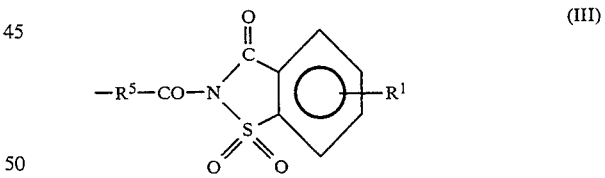
(III)

where $R^1$ and $R^5$ are as defined before can be prepared by reacting an alkali metal derivative of a benzisothiazolinone-1-dioxide having formula (IV) with an acid chloride represented by:

CLCO—$R^5$—COOH  (VI)

where $R^5$ is as defined before, the alkali metal being preferably sodium, but potassium can also be used.

The reaction between the alkali metal derivative and the
acid chloride can be carried out in both cases by refluxing
the alkali metal derivative of the benzisothiazolinone-1-dioxide (IV) with the acid chloride (V) or (VI) in a suitable solvent such as tetrahydrofuran, with stirring. The product formed can then be isolated by filtration and purified by recrystallization from a suitable solvent such as ethanol.

When an acid chloride with formula (VI) is used, the reaction leads to two different products (VII) and (VIII):

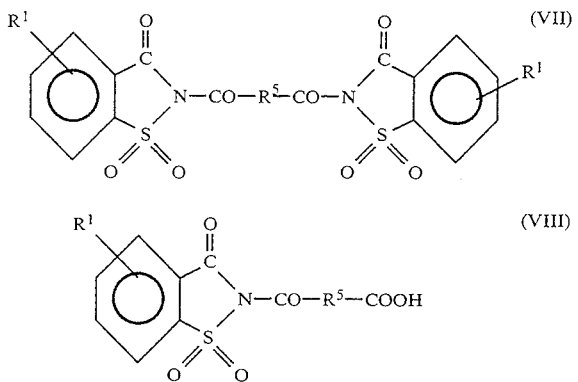

which can be separated from each other by high-pressure liquid chromatography.

The present invention also relates to the new benzisothiazolinone-1-dioxide derivatives themselves with the formula:

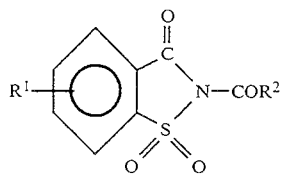

where
R$^1$ is a hydrogen atom or a C$_1$–C$_5$ alkyl or alkoxy group, and
R$^2$ is a monovalent C$_8$–C$_{20}$ alkyl or C$_9$–C$_{20}$ alkenyl group optionally substituted with at least one OH or COOH group, with the proviso that if R$^2$ is unsubstituted alkyl it is C$_{11}$–C$_{20}$ alkyl, or
R$^2$ is a group with the formula:

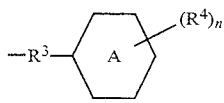

where
R$^3$ is a divalent straight or branched C$_2$–C$_6$ aliphatic group

is an aromatic nucleus
R$^4$ is OH, a C$_1$–C$_4$ alkyl group or a C$_1$–C$_4$ alkoxy group
n is zero or an integer in the range of 1–5, and when n>1, the R$^4$ groups can be different, or else
R$^2$ is a group with the formula:

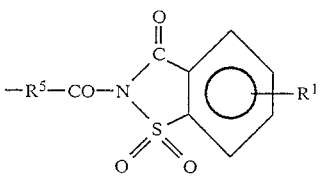

where R$^1$ is as defined before and R$^5$ is a divalent straight or branched C$_8$–C20 aliphatic group.

This invention also embraces methods of treatment comprising administration of compositions of this invention as specified above, especially cosmetic treatment by topical application.

The pharmaceutical compositions of this invention may be solutions, suspensions, emulsions, ointments, creams, powders, lotions or gels, with non-toxic carriers or vehicles and possibly also additives and excipients.

The compounds of the invention can thus be incorporated in conventional excipients such as polyethylene glycols, waxes, fats, stearic substances, talc, alcohols, vegetable oils (e.g. sweet or expressed almond oil), mineral oils, wetting agents, thickeners, preservatives, perfumes and colorants.

These pharmaceutical compositions are intended for oral, parenteral, and—most often—local or topical administration.

These compositions can be used to treat or prevent any undesirable biological or pathological change caused by elastase, such as:
  the degradation of the cutaneous elastic fibres due to ageing or to exposure to the sun
  lysis of the pulmonary elastic fibres due to smoking, ageing and various disorders
  emphysema
  the progressive lysis of the elastic layers in the arterial walls during the development of arteriosclerosis
  arterial disorders due to ageing
  inflammatory foci
  destruction of tissues (e.g. ulcers and necrosis)
  periodontal disorders (degeneration of the gum)
  certain disorders of the bones and joints
  the growth of tumours and the formation of metastases.

As mentioned before, the compounds of the invention can also be used as cosmetics intended to counteract the undesirable effects of elastase on the skin, such as ageing. These cosmetics are essentially intended for application to the skin and can be e.g. solutions, emulsions, creams, ointments, powders, lotions, gels, soaps, milks, face packs, aerosols or bath oils. In the case of emulsions, it is best to use the water-in-oil type, containing the compound of the invention solubilized in the oil phase. These compositions can be prepared by the conventional methods, using the carriers, excipients and additives normally incorporated in such compositions.

The concentration of the new derivative (I) in the composition is chosen according to its activity and the effect required. When intended for local administration once or twice a day, the composition can contain the compound of the invention in a concentration of 0.1 to 5 wt-%.

The cosmetic and pharmaceutical compositions according to the invention that are intended for local application may also contain penetration enhancers or penetration potentiators, which can raise the beneficial effect of the elastase inhibitor by improving its diffusion through the epidermis until it reaches its site of action in the stratum corneum.

These penetration enhancers can act in different ways. For example, they can improve the distribution of the elastase inhibitor on the surface of the skin. Alternatively, they can improve its distribution in the skin after local application, thus promoting the migration of the elastase inhibitor within the stratum corneum. The penetration enhancers may also raise the efficiency of the elastase inhibitor by other mechanisms.

Consequently, the pharmaceutical and cosmetic compositions according to the invention can optionally comprise up to 30 wt-% and preferably 0.1–25 wt-% of a penetration enhancer, examples of which are listed below.

2-methylpropanol-2
2-propanol
ethyl 2-hydroxypropanoate
ethyl polyoxyethylene hexane-2,5-diol ether
di-(2-hydroxypropyl) ether
pentane-2,4-diol
acetone
methyl polyoxyethylene ether
2-hydroxypropionic acid
2-hydroxyoctanoic acid
1-propanol
1,4-dioxan
tetrahydrofuran
1,4-butanediol
propylene glycol dipelargonate
polyoxypropylene 15-stearyl ether
octanol
polyoxyethylene ester of oleyl alcohol
dioctyl adipate
dicapryl adipate
diisopropyl adipate
diisopropyl sebacate
dibutyl sebacate
diethyl sebacate
dimethyl sebacate
dioctyl sebacate
dibutyl suberate
dioctyl azeleate
dibenzyl sebacate
dibutyl phthalate
dibutyl azeleate
ethyl myristate
dimethyl azeleate
butyl myristate
urea
diethyl-m-toluamide
1-dodecylazacycloheptan-2-one
dibutyl succinate
dodecyl phthalate
decyl oleate
ethyl caproate
ethyl salicylate
isopropyl palmirate
ethyl laurate
2-ethylhexyl pelargonate
isopropyl isostearate
butyl laurate
benzyl benzoate
butyl benzoate
hexyl laurate
ethyl caprate
ethyl caprylate
butyl stearate
benzyl salicylate
2-hydroxypropanoic acid
2-hydroxyoctanoic acid.

Other substances that promote the penetration of the active ingredient into the skin include the esters of pyroglutamic acid having the formula:

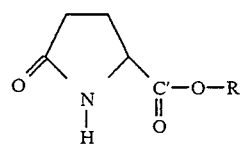

(IX)

where R is either a $C_1$–$C_{30}$ alkyl group or it is the group:

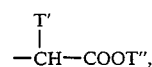

where
T' and T'' (which may be identical or different) represent a hydrogen atom or the following group:

$$[(CH_3)_u, (C_2OH)_v, (CH_2)_w, (CH_3CH_2)_x, (CHOH)_y, (CH=CH)_z]-$$

where
u is zero or 1
v is zero, 1 or 2
w is zero or an integer in the range of 1–21
x is zero or an integer in the range of 1–4
y is zero, 1 or 2
z is zero or an integer in the range of 1–22
and
u+v+w+x+y+z is an integer in the range of 1–22, but when the CH=CH group is present, the total number of carbon atoms in the above group is 10–22.

The following compounds are suitable examples of pyroglutamic acid esters in which the R group, featuring in formula (IX), is a $C_1$–$C_{30}$ alkyl group:

methyl pyroglutamate
ethyl pyroglutamate
n-propyl pyroglutamate
n-butyl pyroglutamate
n-heptyl pyroglutamate
n-octyl pyroglutamate
n-nonyl pyroglutamate
n-decyl pyroglutamate
n-undecyl pyroglutamate
n-dodecyl pyroglutamate
n-tridecyl pyroglutamate
n-tetradecyl pyroglutamate
n-hexadecyl pyroglutamate
n-octadecyl pyroglutamate
n-eicosyl pyroglutamate
isopropyl pyroglutamate
2-methylhexyl pyroglutamate
2-ethylhexyl pyroglutamate
3,7-dimethyloctyl pyroglutamate
2-hexyldecyl pyroglutamate
2-octyldodecyl pyroglutamate
2,4,4-trimethyl-1-pentyl pyroglutamate and
methyloctyl pyroglutamate.

The preferred esters are those in which R is a straight-chain or branched alkyl group with 1-14 and preferably 1-6 carbon atoms. Other preferred examples of pyroglutamic acid esters are those in which R represents the group:

$$-\text{CH.COOT''} \atop | \atop \text{T'}$$

where the symbols T' and T" stand for the group:

$$[(CH_3)_u, (CH_2OH)_v, (CH_2)_w, (CH_3CH_2)_x, (CHOH)_y, (CH=CH)_z]-$$

and which comprise saturated or unsaturated straight-chain or branched $C_1$-$C_{22}$ aliphatic groups such as the alkyl groups: methyl, ethyl, propyl, isopropyl, butyl, isobutyl, n-valeryl, isovaleryl, n-caproyl, n-heptyl, n-caprylyl, n-capryl, lauryl, myristyl, palmityl, stearyl and arachidyl group, and the $C_{10}$-$C_{22}$ alkenyl groups: linoleyl, linolenyl, y-linolenyl, arachidonyl and columbinyl group.

Other examples of these groups comprise hydroxyalkyl radicals with 1-22 carbon atoms, such as the hydroxymethyl, 2-hydroxyethyl, 2-hydroxy-n-propyl, 3-hydroxy-n-propyl, 2-hydroxy-n-butyl, 3-hydroxy-n-butyl, 4-hydroxyl-n-butyl, 5-hydroxy-n-valeryl, 6-hydroxy-n-caproyl, 2,3-dihydroxy-n-propyl, 2,3-dihydroxy-n-butyl and 12-hydroxystearyl group.

This list is not exhaustive, and other alkyl or substituted alkyl groups can be added to it as further examples of T' and T''.

Other specific examples of pyroglutamic acid esters that are particularly suitable for use as penetration enhancers are as follows:

2-(pyroglutamoyloxy)-propionic acid
methyl 2-(pyroglutamoyloxy)-acetate
ethyl 2-(pyroglutamoyloxy)-n-propionate
ethyl 2-(pyroglutamoyloxy)-n-butyrate
ethyl 2-(pyroglutamoyloxy)-isobutyrate
ethyl 2-(pyroglutamoyloxy)-n-valerate
ethyl 2-(pyroglutamoyloxy)-n-caproate
ethyl 2-(pyroglutamoyloxy)-n-heptylate
ethyl 2-(pyroglutamoyloxy)-n-caprylate
ethyl 2-(pyroglutamoyloxy)-n-pelargonate
ethyl 2-(pyroglutamoyloxy)-3-hydroxybutyrate
isopropyl 2-(pyroglutamoyloxy)-n-propionate
isopropyl 2-(pyroglutamoyloxy)-n-caprylate
n-propyl 2-(pyroglutamoyloxy)-n-propionate
n-propyl 2-(pyroglutamoyloxy)-n-caprylate
stearyl 2-(pyroglutamoyloxy)-n-proplonate
12-hydroxystearyl 2-(pyroglutamoyloxy)-n-propionate
stearyl 2-(pyroglutamoyloxy)-n-stearate
palmityl 2-(pyroglutamoyloxy)-n-propionate
linoleyl 2-(pyroglutamoyloxy)-n-propionate
linoleyl 2-(pyroglutamoyloxy)-n-caprylate
lauryl 2-(pyroglutamoyloxy)-n-caprylate
stearyl 2-(pyroglutamoyloxy)-n-caprylate
glyceryl mono-2-(pyroglutamoyloxy)-n-propionate
glyceryl mono-2-(pyroglutarnoyloxy)-n-caprylate, and
glyceryl di-2-(pyroglutamoyloxy)-n-propionate.

These lists of specific examples of pyroglutamic acid esters are not exhaustive, and many other examples with the overall structure of these esters could be mentioned. Other examples of penetration enhancers are as follows:

dimethylsulphoxide
N,N-dimethylacetamide
N,N-dimethylformamide
2-pyrrolidone
1-methyl-2-pyrrolidone
5-methyl-2-pyrrolidone
1,5-dimethyl-2-pyrrolidone
1-ethyl-2-pyrrolidone
phosphine oxides
sugar esters, and
tetrahydrofurfuryl alcohol.

Other features and advantages of the present invention will emerge from the following non-limitative examples, given here to illustrate the present invention.

EXAMPLE 1

Preparation of 2-lauroylbenzisothiazolinone-1-dioxide 21.8 g (0.1 mole) of lauroyl chloride and 22.66 g (0.11 mole) of dry sodium benzisothiazolinone-1-dioxide were refluxed for 4 h in 80 ml of tetrahydrofuran, with mechanical stirring. The reaction mixture was filtered, the filtrate was concentrated under vacuum, and the product was recrystallized from ethanol and dried in air. This gave 30 g of 2-lauroylbenzisothiazolinone-1-dioxide (m.p. 85° C.).

EXAMPLE 2-6

The method described in Example 1 was used to prepare various compounds with formula I, in which the groups denoted by $R^1$ and $R^2$ are shown in Table 1. The acid chloride used here was myristoyl chloride in Example 2, palmitoyl chloride in Example 3, stearoyl chloride in Example 4, decanoyl chloride in Example 5 and undecenoyl chloride in Example 6. The melting points of the compounds obtained are given in Table 1.

EXAMPLE 7

Preparation Of
2-[(3,4)-dimethoxycinnamoyl]-benzisothiazolinone-1-dioxide 227 g (0.1 mole) of 1,4-dimethoxycinnamoyl chloride and 22.66 g (0.11 mole) of anhydrous sodium benzisothiazolinone-1-dioxide were refluxed for 5 h in 150 ml of dry tetrahydrofuran, with mechanical stirring. The reaction mixture was then filtered, the filtrate was concentrated under vacuum, and the product obtained was recrystallized from ethanol, giving 22 8 of 2-[(3,4)-dimethoxycinnamoyl]-benzisothiazolinone-1-dioxide (m.p. 171 ° C.) .

EXAMPLE 8-10

The method described in Example 7 was used to prepare various compounds with formula I, in which the groups denoted by $R^1$ and $R^2$ are shown in Table 1. The acid chloride used here was cinnamoyl chloride in Example 8, dihydrocinnamoyl chloride in Example 9, and p-methoxyphenylbutyryl chloride in Example 10. The melting points of the compounds obtained are given in Table 1.

EXAMPLE 11

Preparation of compounds (VIIa) and (VIIIA): 1,10-decanedioyl-bis-(2-benzisothiazolin-3-oxo-1,1-dioxide and 1-carboxynonanoyl-10-(2-benzisothiazolin-3oxo-1,1-dioxide)

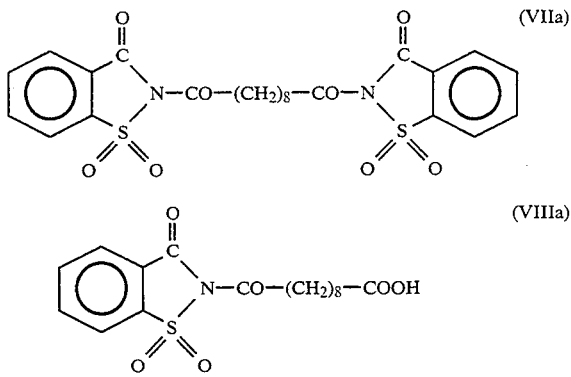

A mixture of 9 g (0.05 mole) of sebacoyl chloride and 20.6 g (0.1 mole) of sodium benzisothiazolinone-1-dioxide was refluxed for 4 h. The reaction mixture was then filtered, and the filtrate was concentrated under vacuum. The resulting compounds VIIa and VIIIa were separated by preparative high-pressure liquid chromatography, using a reversed-phase C18 column and a water/acetonitrile gradient. The $R_f$ value of compounds (VIIa) and (VIIIa) was respectively 0.8 and 0.2 when eluted on silica with a 99:1 chloroform-methanol mixture (by volume).

Both the mixture of compounds VIIa and VIIIa and each of them separately can be used as an elastase inhibitor.

EXAMPLE 12

Inhibition of human leucocytic elastase

The inhibition test was carried out by using succinyl-trialanine p-nitroanilide as a synthetic substrate. Human leucocytic elastase, used at a concentration of 1 $\mu$g/ml, was first pre-incubated for 15 min with the compounds of the invention, used at a concentration of 0.5, 5, 10, 25 and 50 $\mu$g/ml. These compounds were added in the form of a solution in acetone, the final acetone concentration of the reaction mixture being 1%.

The degree of hydrolysis of the substrate was determined by measuring the amount of p-nitroaniline released, using a Philips PO 8700 spectraphotometer at 410 nm. The 50% inhibitory concentration (IC$_{50}$) in mole/liter was then determined by a graphical method, using the inhibition values obtained with the different concentrations of the substrate and the inhibitor. Table 1 shows the IC$_{50}$ values obtained for the compounds of the invention prepared in Examples 1–5. It can thus be seen that the inhibitory action of these compounds increases with the number of carbon atoms in the $R^2$ group on going from C$_9$ to C$_{17}$.

TABLE I

| Example No. | $R^1$ | $R^2$ | M.p. °C. | IC$_{50}$ mole/l |
|---|---|---|---|---|
| 1 | H | C$_{11}$H$_{23}$ | 85 | $1.1 \times 10^{-5}$ |
| 2 | H | C$_{13}$H$_{27}$ | 89 | $9.2 \times 10^{-6}$ |
| 3 | H | C$_{15}$H$_{31}$ | 94 | $2.1 \times 10^{-6}$ |
| 4 | H | C$_{17}$H$_{35}$ | 90 | $4.7 \times 10^{-6}$ |

TABLE I-continued

| Example No. | $R^1$ | $R^2$ | M.p. °C. | IC$_{50}$ mole/l |
|---|---|---|---|---|
| 5 | H | C$_9$H$_{19}$ | 84 | $8.6 \times 10^{-5}$ |
| 6 | H | C$_{10}$H$_{19}$ | 75 | $7.5 \times 10^{-5}$ |
| 7 | H | —CH=CH—C$_6$H$_3$(OCH$_3$)$_2$ | 171 | $5 \times 10^{-6}$ |
| 8 | H | —CH=CH—C$_6$H$_5$ | 222 | $9 \times 10^{-5}$ |
| 9 | H | —CH$_2$—CH$_2$—C$_6$H$_5$ | 142 | $4.8 \times 10^{-5}$ |
| 10 | H | —(CH$_2$)$_3$—C$_6$H$_4$(OCH$_3$) | 142 | $3.6 \times 10^{-5}$ |

EXAMPLE 13

Protective action of 2-lauroylbenzisothiazolinone-1-dioxide on elastin and its inhibition of human leucocytic elastase Three series of tests were carried out here to illustrate the manner by which the compound prepared in Example 1 inhibits the elastase.

1) Inhibitory action. The elastase, used in a concentration of 1 $\mu$g/ml, was incubated for 10 min with different amounts of 2-lauroylbenzisothiazolinone-1-dioxide in a 100-mM tris-HCl buffer (pH 8.4) containing 0.01% of BriJ 35 and 0.01% of NaN$_3$. Tritiated insoluble elastin extracted from the nuchal ligament was then added in a concentration of 75 $\mu$g/ml, corresponding to a radioactivity level of $2.2 \times 10^6$ counts per minute (cpm) per ml.

2) Protective action. The substances and concentrations were the same as above, but the insoluble elastin was incubated with 2-lauroylbenzisothiazolinone-1-dioxide for 30 min before the introduction of human leucocytic elastase.

3) Third series. Again the same substances and concentrations were used as before, but the insoluble elastin was first incubated with 2-lauroylbenzisothiazolinone-1-dioxide for 10 min. The mixture was then centrifuged, the supernatant was discarded, and the residue was suspended in the buffer that contained human leucocytic elastase.

The degree of the hydrolysis of elastin was calculated in all three cases after incubation with elastase for 7 h at 37° C. by determining the radioactivity in the solubilized peptides derived from the elastin.

The aim of the first series was to determine the direct ability of 2-lauroylbenzisothiazolinone-1-dioxide to inhibit the activity of human leucocytic elastase. The results show that, when used in a concentration of 45 $\mu$g/ml, 2-lauroylbenzisothiazolinone-1-dioxide inhibits the elastin-cleaving activity of human leucocytic elastase by 80%, the value of IC$_{50}$ being $7.5 \times 10^{-5}$ M.

The second and third series of investigations showed that the compound of the invention also protects the insoluble elastic fibres from the action of human leucocytic elastase with a maximum inhibition of 50% when used in a concentration of 50–100 $\mu$g/ml, the IC$_{50}$ value being $1.3$–$2.9 \times 10^{-4}$M.

EXAMPLE 14

Protective action of 2-lauroylbenzoisothiazolinone-1-dioxide on the elastin in rabbit skin Frozen biopsy specimens of rabbit skin having a thickness of 6μ were treated either with human leucocytic elastase in a concentration of 15 μg/ml or with a mixture of this and 2-lauroylbenzisothiazolinone-1-dioxide, prepared in Example 1 and used in a concentration of 350 μg/ml.

The segments of rabbit skin were incubated for 1.5 h at 37° C. In the control experiment, they were incubated only with the buffer (100-mM tris-HCl, 0.1% of Brim 35, pH 8) under the same conditions.

Thin sections of the skin specimens were then fixed for 2 min in 95% ethanol and stained for 3 h by a modified Verhoeff method, described by Godeau et al. [cf. Pathol. Biol., 32 (1984) pp. 215–6]. After a suitable contrast treatment, the surface density of the elastic fibres was determined by automatic image analysis, carried out directly on the microscope slides.

In the absence of elastase, the volume fraction V occupied by the cutaneous elastic fibres was 6.25±0.5%. After treatment with human leucocytic elastase, this value was only 4.1±0.8%. When the elastase was first incubated with 2-lauroylbenzisothiazolinone-1-dioxide, however, the value of V was 6.00±1%, which indicates a virtually complete (96%) protection from the action of elastase.

EXAMPLE 15

Determination of the inhibition of other serine-containing proteases

The inhibition exerted by the following two compounds on serine-containing proteases other that, human leucocytic elastase was determined in this Example:

2-butyryl-benzisothiazolinone-1-dioxide (B) and
2-palmitoyl-2-benzisothiazolinone-1-dioxide (P).

More specifically, the activity of a) pig pancreatic elastase, b) trypsin, c) thrombin and d) plasmin was determined in the presence of these inhibitors and of the synthetic substrates: a) succlnyltrialanine p-nitroanilide, b) N-benzoyl-DL-arginine p-nitroanilide, c) N-p-tosyl-gly-pro-arg p-nitroanilide and d) N-p-tosyl-gly-pro-lys p-nitroanilide, respectively.

Each enzyme was first incubated for 15 min with 0–50 μg/ml of compound B or P mentioned above, which had been dissolved in acetone as in the test with burned leucocytic elastase, the final concentration of this solvent in the reaction mixture being 1%.

The appropriate substrate was then added to each enzyme, and its hydrolysis was monitored with a Philips 8700 spectraphotometer at 410 nm by measuring the amount of p-nitroaniline appearing in the medium.

The results were used to plot the inhibition of the enzymatic activity against the amount of inhibitor present in tile medium. These curves were then used to find the median inhibitory concentration ($IC_{50}$) in mole/l, which inhibits 50% of the enzymatic activity.

Inhibition of human leucocytic elastase was also determined, as in Example 12.

To be able to compare the inhibitory power of the compounds tested on the various enzymes used, the $E/IC_{50}$ value was calculated, where E is the concentration of the enzyme in the reaction mixture (also expressed in mole/l). The higher the value of this quotient, the stronger the inhibitory activity, and therefore the lower the number of moles of the inhibitor that are needed to obtain a 50% inhibition for the same number of moles of the enzyme.

The results listed in Table 2 show that palmitoylbenzisothiazolinone-1-dioxide is a better inhibitor than butyrylbenzisothiazolinone-1-dioxide, irrespective of the enzyme used. Furthermore, these inhibitors show different specificities for the different serine proteases employed. Thus, 2-butyrylbenzisothiazolinone-1-dioxide inhibits human leucocytic elastase and pi$_E$ pancreatic elastase more strongly than it inhibits thrombin; it has no effect on plasmin and in fact activates trypsin. 2-Palmitoyl-2-benzisothiazolinone-1-dioxide inhibits human leucocytic elastase, pig pancreatic alasrase and trypsin 20–40 times as strongly as it inhibits thrombin. This indicates that the compound according to the invention, i.e. 2-palmitoyl-benzisothiazolinone-1-dioxide, is much more efficient than 2-butyrylbenzisothiazolinone-1-dioxide, in which the hydrocarbon chain contains fewer than nine carbon atoms.

TABLE 2

|  | $E/IC_{60}$ | |
| --- | --- | --- |
|  | Butyrylbenziso-thiazolinone-1-dioxide | Palmitoylbenziso-thiazolinone-1-dioxide |
| Human leucocytic elastase | $7 \times 10^{-4}$ | $8.1 \times 10^{-3}$ |
| Pig pancreatic elastase | $3.7 \times 10^{-6}$ | $3.2 \times 10^{-3}$ |
| Trypsin | activator | $4.2 \times 10^{-3}$ |
| Thrombin | $2.3 \times 10^{-6}$ | $1.8 \times 10^{-4}$ |
| Plasmin | inactive |  |

Examples 16–21 illustrate some cosmetic compositions containing elastase inhibitors according to the present invention.

EXAMPLE 16

This Example illustrates a gel for the treatment of hair, this product containing the compound mentioned in Example 2, i.e. 2-myristoylbenzisothiazolinone-1-dioxide, and having the following composition.

|  | Amount, wt-% |
| --- | --- |
| Emulsifier | 20.00 |
| Silicone oil | 20.00 |
| Inhibitor from Example 2 | 2.00 |
| Sodium hydroxide | 4.55 |
| 1,3-Butanediol | 11.00 |
| Lactic acid | 5.00 |
| Water | 37.45 |
|  | 100.00 |

EXAMPLE 17

This Example illustrates a face pack containing the inhibitor used in Example 4, i.e. 2-stearoylbenzisothiazolinone-1-dioxide, and having the following composition, the product being prepared by mixing the ingredients together.

|  | Amount, % |
| --- | --- |
| Kaolin | 35.00 |
| Bentonite | 5.00 |
| Cetyl alcohol | 2.00 |
| Potassium dodecyl sulphate | 1.00 |
| Glycerol | 10.00 |
| Nipagin M | 0.10 |

-continued

|  | Amount, % |
|---|---|
| Inhibitor from Example 4 | 5.00 |
| Perfume | 5.00 |
| Water | 36.90 |
|  | 100.00 |

EXAMPLE 18

This Example illustrates a lotion suitable for the treatment of nails, containing the inhibitor used in Example 6, i.e. 2-undecenoylbenzisothiazolinone-1-dioxide, and having the following composition, the lotion (which had a pH of 4.4) being prepared by homogenizing the mixture of its ingredients.

|  | Amount, % |
|---|---|
| Inhibitor from Example 6 | 6.00 |
| Sodium hydroxide | 1.50 |
| Ethanol | 10.00 |
| 1,2-Propanediol | 55.00 |
| Water | 27.50 |
|  | 100.00 |

EXAMPLE 19

This Example illustrates a skin cream formed by a water-in-oil emulsion and containing the inhibitor from Example 1, i.e. 2-lauroylbenzisothiazolinone-1-dioxide in its continuous oil phase, the composition of the cream being as follows.

|  | Amount, wt-% |
|---|---|
| Silicones | 24.00 |
| Sodium chloride | 2.00 |
| Inhibitor from Example 1 | 3.00 |
| Lactic acid | 5.00 |
| Humectants | 5.00 |
| Bleaching agent | 0.15 |
| Preservatives | 0.05 |
| Oil of evening primrose | 3.00 |
| Sunscreens | 4.00 |
| Bactericides | 0.30 |
| Water | 53.50 |
|  | 100.00 |

This skin cream, which had a pH of 4, was prepared by mixing the silicones, the bleaching agent and the preservatives together, adding a mixture of the other ingredients in small portions, and homogenizing the product.

EXAMPLE 20

This Example illustrates a water-in-oil type cream, which contained sunscreens in its continuous oil phase, together with the inhibitor from Example 7, i.e. 2-(3,4-dimethyoxycinnamoyl)-benzisothiazolinone-1-dioxide. This cream had the following composition.

|  | Amount, % |
|---|---|
| Silicones | 24.00 |
| Humectants | 10.00 |
| Bleaching agent | 0.15 |
| Preservatives | 0.05 |
| Oil of evening primrose | 3.00 |
| Sunscreens | 4.00 |
| Bactericides | 0.30 |
| Inhibitor from Example 7 | 1.00 |
| Ammonium hydroxide | 2.00 |
| Ammonium chloride | 2.00 |
| Lactic acid | 5.00 |
| Water | 48.50 |
|  | 100.00 |

EXAMPLE 21

This Example illustrates a water-in-oil type cream that contained sunscreens in its continuous oil phase, together with the inhibitor with formula (VIIa) from Example 11, i.e. 1,10-decanedioyl-bis-(benzisothiazolin-3-oxo-1,1-dioxide), the cream having the following composition.

|  | Amount, % |
|---|---|
| Silicones | 24.00 |
| Humectants | 10.00 |
| Bleaching agent | 0.15 |
| Preservatives | 0.05 |
| Oil of evening primrose | 3.00 |
| Sunscreens | 4.00 |
| Bactericides | 0.30 |
| Inhibitor from Example 11 (with formula VIIa) | 1.00 |
| Ammonium hydroxide | 2.00 |
| Ammonium chloride | 2.00 |
| Lactic acid | 5.00 |
| Water | 48.50 |
|  | 100.00 |

We claim:

1. A composition comprising:
   (i) an elastase inhibitor which is at least one benzisothiazolinone-1-dioxide derivative having the formula:

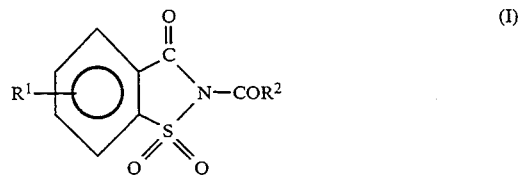

where
R$^1$ is a hydrogen atom,
R$^2$ is a monovalent C$_{11}$–C$_{19}$ alkyl or alkenyl group; and
   (ii) a pharmaceutically or cosmetically acceptable carrier.

2. A composition according to claim 1, wherein R$^2$ is a C$_{13}$–C$_{17}$ alkyl or alkenyl group.

3. The composition according to claim 2, wherein COR$^2$ is a palmitoyl radical.

4. The composition according to claim 1, wherein the elastase inhibitor is present in an amount from 0.1 to 5% by weight.

5. A method for cosmetically treating human skin to prevent signs of ageing, comprising applying topically to the skin a composition comprising:
   (i) an elastase inhibitor which is at least one benzisothiazolinone-1-dioxide derivative having the formula:

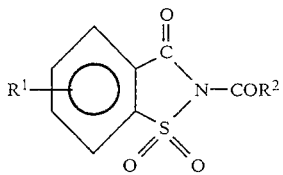 (I)

where

R¹ is a hydrogen atom,

R² is a monovalent $C_{11}$–$C_{19}$ alkyl or alkenyl group; and (ii) a pharmaceutically or cosmetically acceptable carrier.

6. The method according to claim 5, wherein R² is a $C_{13}$–$C_{17}$ alkyl or alkenyl group.

7. The method according to claim 6, wherein COR² is a palmitoyl radical.

8. The method according to claim 5, wherein the elastase inhibitor is present in an amount from 0.1 to 5% by weight.

* * * * *

UNITED STATES PATENT AND TRADEMARK OFFICE
CERTIFICATE OF CORRECTION

PATENT NO. : 5,411,978
DATED : May 2, 1995
INVENTOR(S) : Robert Ladislas, et al

It is certified that error appears in the above-indentified patent and that said Letters Patent is hereby corrected as shown below:

Title page, item [75] "Robert Ladislas" should read —Ladislas Robert— item [19] "Ladislas et al." should read —Robert et al.—

Signed and Sealed this

Nineteenth Day of September, 1995

*Attest:*

BRUCE LEHMAN

*Attesting Officer*    *Commissioner of Patents and Trademarks*